United States Patent [19]

Habermehl et al.

[11] 4,283,629

[45] Aug. 11, 1981

[54] METHOD AND APPARATUS FOR TESTING MATERIALS SUCH AS DISEASE IN LIVING TREES

[75] Inventors: Adolf Habermehl, Zum Lahnberg 44, D-3550 Marburg, Lahn, Fed. Rep. of Germany; Hans-Werner Ridder, Marburg, both of Fed. Rep. of Germany

[73] Assignee: Adolf Habermehl, Marburg, Fed. Rep. of Germany

[21] Appl. No.: 23,265

[22] Filed: Mar. 23, 1979

[30] Foreign Application Priority Data

Oct. 26, 1978 [DE] Fed. Rep. of Germany ....... 2846702

[51] Int. Cl.³ .............................................. G03B 41/16
[52] U.S. Cl. ................................. 250/445 T; 250/523
[58] Field of Search ............... 250/445 T, 523, 358 R, 250/360

[56] References Cited

U.S. PATENT DOCUMENTS

| | | | |
|---|---|---|---|
| 3,946,234 | 3/1976 | Hounsfield | 250/445 T |
| 4,084,094 | 4/1978 | Froggatt | 250/445 T |

*Primary Examiner*—Craig E. Church

[57] ABSTRACT

The non-destructive testing of materials such as for disease in living trees is carried out by determining at each of a plurality of positions in a given cross-section of said material to be tested the coefficient of absorption of a predetermined radiation source, and converting said coefficient of absorption at each of said position into a computerized tomographic display. The radiation source is selected from the group consisting of gamma, x-ray, and neutron radiation.

22 Claims, 12 Drawing Figures

FIG.7

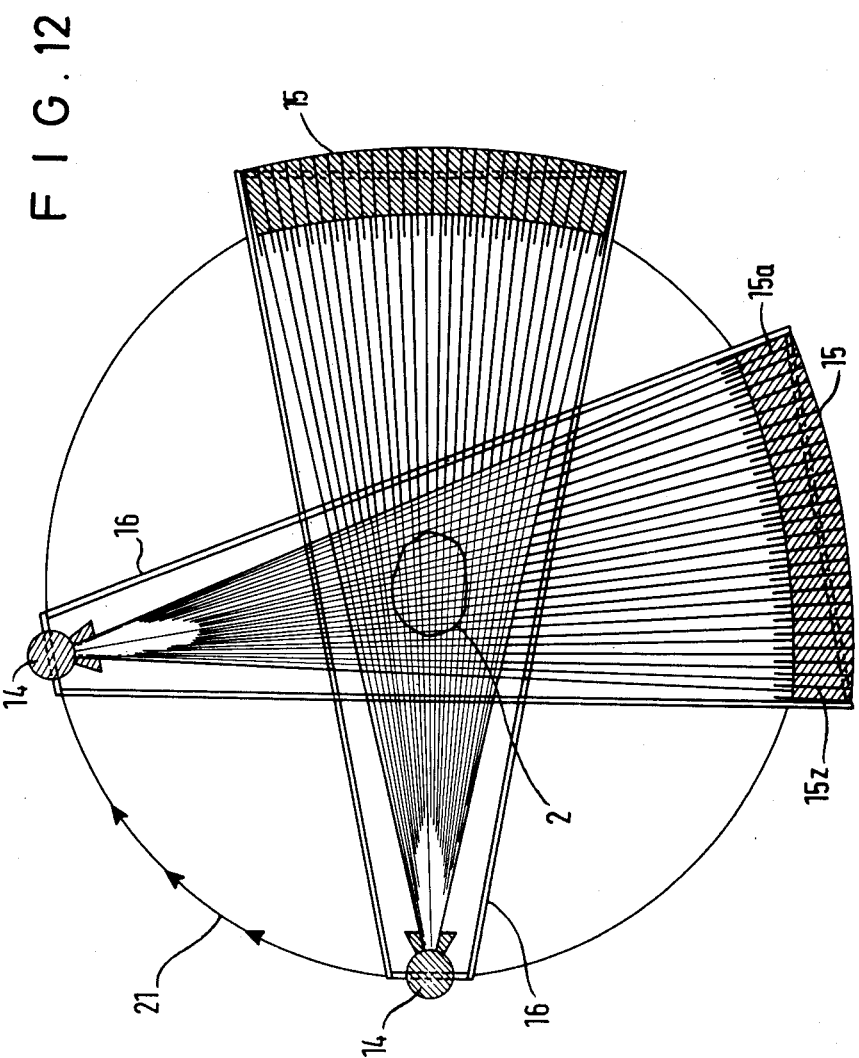

METHOD AND APPARATUS FOR TESTING MATERIALS SUCH AS DISEASE IN LIVING TREES

BACKGROUND OF THE INVENTION

The present invention relates to a method and apparatus for non-destructive materials testing, in particular for the detection of red rot and other tree diseases in the trunks of living trees.

The increasing contamination of the air and the growing mechanization of the forest industry have led to an increase in tree disease and to an intensified attack by pests. In the Federal Republic of Germany alone losses of about DM 150 million a year are estimated. These losses are even considerably higher in more heavily forested regions; for example, in Scandinavia they are estimated at about DM 200 to 250 million annualy. In order to keep the ecological and economic losses in bounds it is necessary to recognize and combat them as early as possible.

One particular tree disease which causes much damage is red rot which occurs in needle trees and is caused by the fungus Fomes Annosus. This fungus attacks mainly needle trees and rarely leaf trees. Of the coniferous trees, spruce and pine are primarily endangered. The larch, Douglas fir and other kinds are only secondarily attacked. The fungus finds favorable growth conditions predominantly in standing trees and causes a root rot which, in the pine, leads to the tree dying in its youth while bringing about, in the spruce, a gradually increasing destruction of the wood inside the trunk which greatly reduces the value of its lumber, but does not threaten the life of the tree directly. For this reason, the rot is not easily recognizable from the exterior, although the interior wood is being destroyed or is already destroyed and the destruction is continuing.

Because of these damaging effects the fungus fomes annosus is one of the most significant fungi for the forestry industry since the damage brought about by it can be very considerable, be it that in young plants do not develop at all or that in older standing trees with diseased roots are easily uprooted by the wind. In addition, spruce with rotten trunks often suffer broken trunks. This alone may cause considerable lumber losses. But the most important damage is done by the fungus directly in the wood of the trunk. Since red rot moves upwardly from the bottom of the trunk, it is precisely the economically most valuable parts of the wood which are damaged first so as to be no longer usable as building or sawed lumber, although it can only at best be processed for cellulose production or used as fire wood.

If the disease is recognized in time, damage caused by the rot rising in the trunk can be reduced or kept in bounds by early cutting. This requires proof of the disease on the standing tree, if possible without injuring the tree. However, to obtain this proof in a whole stand or in an individual case is not easy. To date, the ultimate extent and spread of the disease can be determined exactly in the individual case only be felling the tree, and in a stand only by examining a sufficient number of felled sample trees.

Another detection method which avoids the above mentioned, relatively expensive sample fellings is the drill chip analysis, which reveals information on the degree of rotting by way of the coloration of a drill chip taken. The technique is described by S. Lange in the journal "Forstw. Centralbl." 78 (1959), pages 174/180. Generally, this requires several drillings for a reliable diagnosis. The injuries inflicted by this process can then again become the starting point of wound rot or trunk rot.

In another method the resistance of the wood to electric current pulses at different trunk depths is measured. This method is described in the journal "Canadian Journal of Forest Research" 2 (1972) pages 54/56. Holes are also drilled into the trunk and then a probe with two electrodes is inserted into the drill holes. Current is supplied via two probe tips and the resistance offered by the wood to current pulses is measured and recorded as a function of the location of the probe tips. The resistance depends on the ion concentration in the wood, and since rotten wood contains cations to a greater extent than anions, the electrical resistance drops across the rotted areas. The intensity of the red rot and the location of the spot where the resistance drops can only be approximated by this method. This method, too, has the disadvantage of damaging the trees and thus making them susceptible to diseases.

Also known are sonic test methods by which reflected sonic pulses are analyzed by appropriate test setups. They are described in "Mitt.Dtsch.Ges.f. Holzforsch." 38 (1955), pages 8 to 11. Some of these methods measure the reflected residual energy of supersonic waves, others the attenuation as a function of frequency. Subsequently, certain conclusions as to the state of rot are drawn from the measured values. These sonic test methods are able to reveal relatively little information only because the differences in the sound intensity between healthy and diseased trunks are too small. By the same token, when measuring the attenuation as a function of frequency, very small differences only can be detected, with test results widely scattered. In addition, problems arise from coupling the sound transmitter to the trunk. The coupling must be very good and requires an absolutely plane surface. Therefore, for an unobjectionable measurement the standing trunk must be injured so that the operating mode of this method is not entirely non-destructive.

In contrast to these methods, which always require a more or less severe injury of the tree, the non-destructive test methods are of greater interest because they do not damage the wood part of the tree.

One such non-destructive test method is x-raying, as described in the journal "Forstw. Centralbl." 78 (1959), pages 174 to 180. But this method is too expensive and unsuited for forestry practice, the apparatus required being too huge and unwieldy in particular.

Finally, a method has been proposed, as described in "For. Sci." 5 (1959), pages 37 to 47, and in "Wood Sci. and Techn." 2 (1968) pages 128 to 137, which operates with the radioactive isotope thulium as a radiation source and in which the blackening of a film disposed on the tree trunk side opposite the radiation source, by the rays emanating from the radioactive radiation source and penetrating the tree trunk is measured. Depending on the thickness of the tree, this requires an exposure time of 1.5 minutes to 15 hours. After development of the exposed film the blackening as a function of location is measured, and on the basis of this blackening, a curve of rotted spots can be identified by comparison with normal curves of healthy trees.

X-ray methods and methods using radioactive isotopes, in principle, measure the weakening of rays of a certain energy range when passing through the wood. The parameter describing this weakening quantitatively is the weakening coefficient $\mu$. On the one hand, it is a function of the energy of the radiation used, and on the other, of the weakening substance S. Therefore, at a fixed radiation energy E, the weakening coefficient $\mu$ is a suitable numerical measure for the description of certain characteristics of the penetrated substance S. Extensive measurements and investigations of the absorption of gamma rays in wood have shown that the absorption coefficient $\mu$ is a suitable means of obtaining information as to whether the wood is healthy or changed in its chemical composition by the red rot, and thus also in its physical-technical parameters.

According to the hitherto known methods, the degree of weakening, which equals the ratio of the weakened radiation I to the unweakened radiation $I_o$, and the thickness of the irradiated layer d, which can be measured externally relatively simply, are the factors determining the total absorption, which equals the integral along the direction of radiation over the numerically non-constant values of the absorption coefficient in the interior of the trunk and by means of which it can be determined numerically whether homogeneous, sound wood or partly red rotted wood is involved.

This method, which is based on the determination of the means absorption coefficient $\mu_{ges}$, makes it possible to estimate cavities in the trunk, and in the presence of certain conditions the size of the cavity can be determined in many cases from such extrenal measurements. However, the exact location of a cavity cannot be fixed definitely with such an absorption measurement. Results utilizable in practice can be obtained only under the assumption that a defect found is located in the center of the trunk, but in reality the location of such a defect is uncertain. Consequently, this method is too inaccurate and too unreliable.

The invention now makes available a method and apparatus for its execution which makes possible an accurate and nondestructive as well as reliable materials test, in particular for the detection of red rot and other tree diseases in the trunks of living trees.

SUMMARY OF THE INVENTION

According to the present invention, a plurality of position-dependent determination of the coefficient of absorption of the material to be tested, in particular of the trunk of a living tree, for a predetermined kind of radiation, preferably for gamma radiation and/or neutron radiation, is carried out in a cross-section of the material by means of computer tomography.

Heretofore, computer tomography has been applied only in the completely different field of human medicine and described, for example, in the article "Siretom—a skull traversal layer apparatus with computer" by K. Fuhrer et al, published in the journal "Electromedica" $\frac{2}{3}$ (1975), pages 48 to 55, and in the article by G. N. Hounsfield, "Computerized transverse axial scanning (tomography)" published in the journal "Brit. Journ. of Radiology" 46 (1973), pages 1016 to 1022. The disclosure of these printed publications are herewith made a part of the present application.

The apparatus for the execution of the method according to the invention, comprises a supporting frame for the measuring device of a computer tomography system by which the measurement of the coefficient of absorption of the material to be tested for a predetermined kind of radiation, preferably gamma radiation and/or neutron radiation is provided. The supporting frame is arrangeable so as to surround and is preferably fastenable to the material to be tested, in particular the trunk of a living tree.

Full details of the features of the present invention are disclosed in the following description of the method and apparatus and of some particularly preferred embodiment examples which are shown in detail in the accompanying drawings:

BRIEF DESCRIPTION OF THE DRAWINGS

FIG. 7 is an example of a number matrix of the coefficients of absorption on the transverse section of a tree trunk;

FIG. 12 is a second modified embodiment of the radiation measuring arrangement according to FIGS. 3 and 4.

DESCRIPTION OF THE INVENTION

Briefly, computer tomography can be used to determine the coefficient of absorption for penetrating radiation and illustrates in suitable manner its distribution as a function of the position coordinates. The coefficient of absorption of a substance for ionizing radiation depends on the energy of the radiation itself and on the composition of the weakening substance and is thus a numerical measure for the characterization of the physical properties of the material penetrated. A change in the coefficient of absorption due to rot—or other factors—can, therefore, be detected by computer tomography.

In principle, the coefficient of absorption can be determined as follows:

The weakening of a parallel bundle of ionizing rays by a homogeneous layer of the thickness d and the coefficient of absorption $\mu$ is $$I = I_o \cdot e^{-\mu d}.$$

Therein, I is the weakened intensity of the rays and $I_o$ the unweakened intensity of the beam of rays. Since, in the problem at hand, the thickness d is measurable externally in addition to I and $I_o$ the coefficient of absorption of an homogeneous material can be determined from these measurements according to $$\mu = (1/d) \cdot \ln(I/I)o.$$

For the case occurring in practice where the material, the trunk, is heterogeneous so that the coefficient of absorption is position-dependent, a mean absorption for each irradiation direction can be computed by this simple method. While this mean coefficient of absorption permits estimates and hints of cavities and rot zones in the trunk, however, the distribution of the coefficient of absorption in radiation direction remains unknown due to the basic difficulties mentioned.

The problem of also fixing the location of a defect in radiation direction, or generally of determining the coefficient of absorption inside the trunk as a function of position is rendered more difficult in that, due to the position dependence of $\mu(x,y)$, $$I = I_o \cdot e^{-s \int \mu(x,y) \, ds}$$

This leads to $$\ln(I/I)o = s \int \mu(x,y) \, ds$$

s being a function of irradiation.

This equation can no longer be easily solved with respect to $\mu(x,y)$.

But a position-dependent determination of the coefficient of absorption can be achieved by computer tomography. Through external measurements and subsequent mathematical processes, which can be carried out with the help of a computer only, however, the coefficient of absorption in a thin layer of the object for each location is determinable even if this location is unaccessible to direct measurement. It is, therefore, also a method suited for localizing red rot spots in inaccessible locations, such as in the interior of standing trunks, via the coefficient of absorption.

Figure 1:
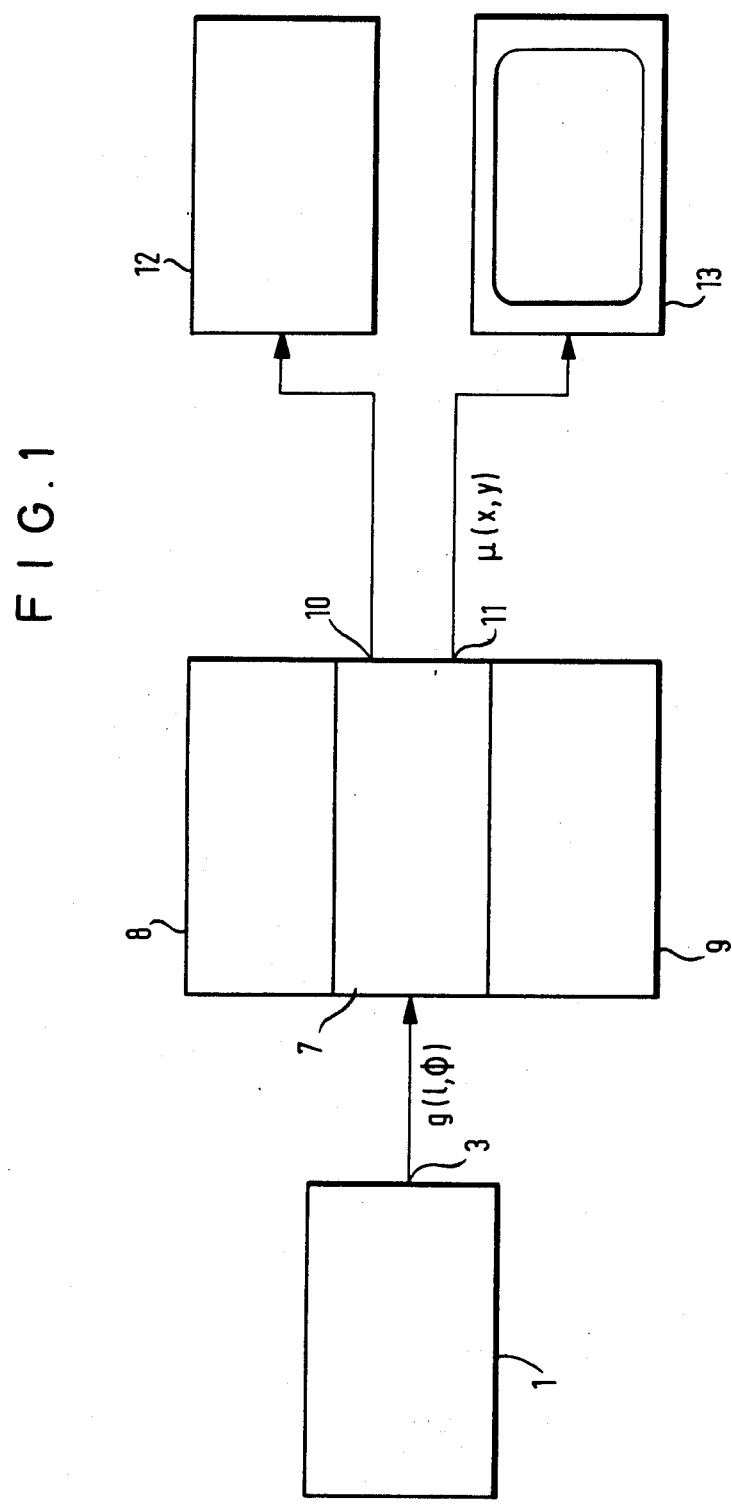
FIG. 1 is a schematic block diagram of a device for the execution of computer tomography.
Figure 2:
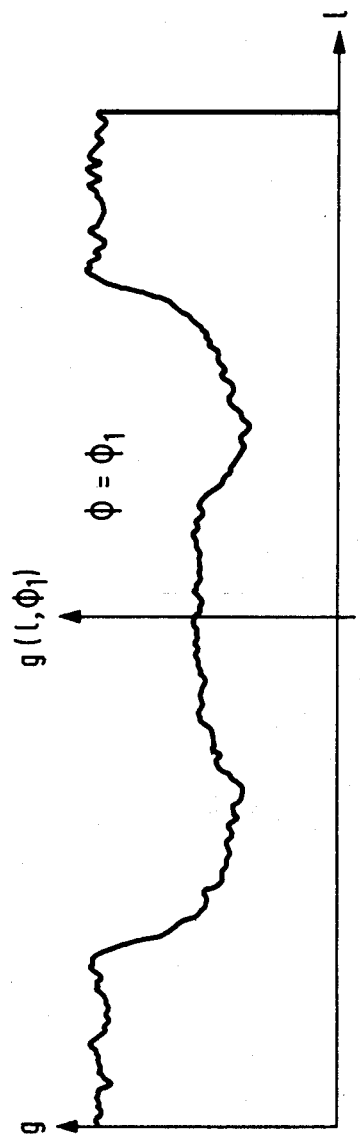
FIG. 2 is a graph of an example of a unidimensional profile as available at the output of the measuring system according to FIG. 1.
Figure 3:
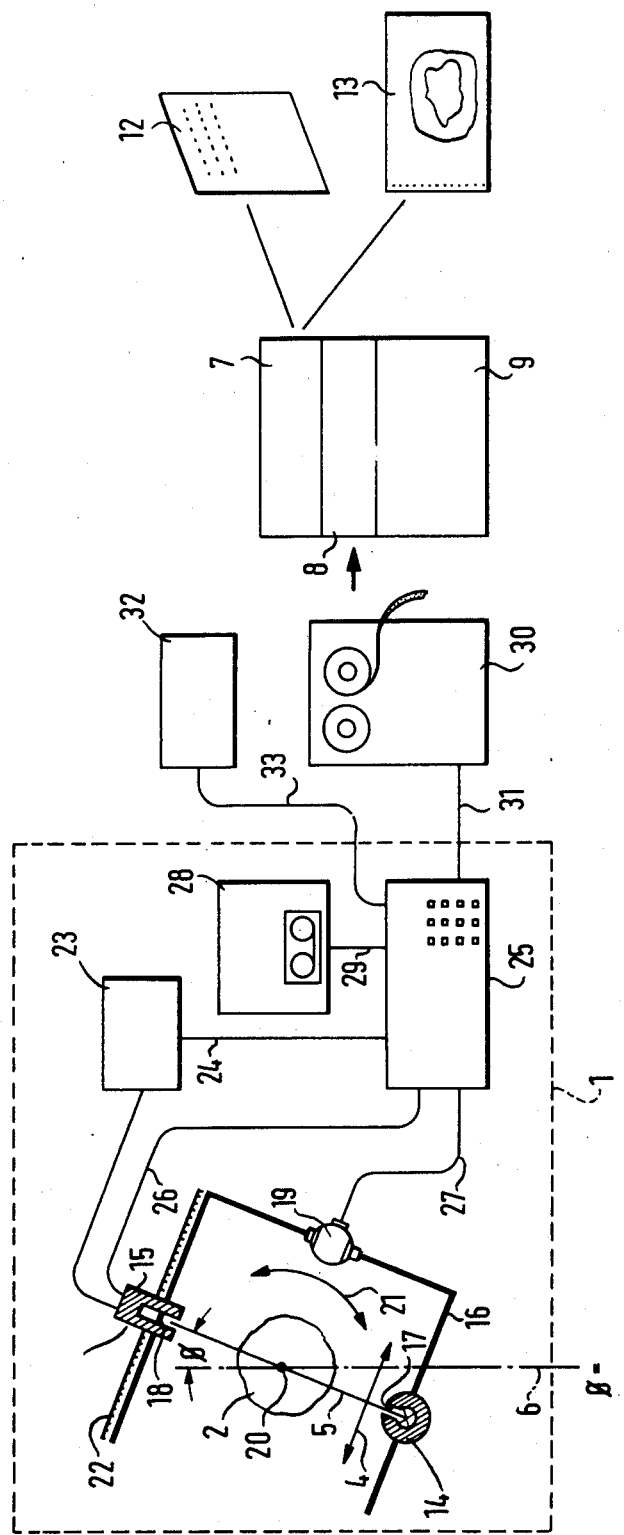
FIG. 3 is a more detailed block wiring diagram of a mobile device according to the invention and of the associated stationary system components.
Figure 4:
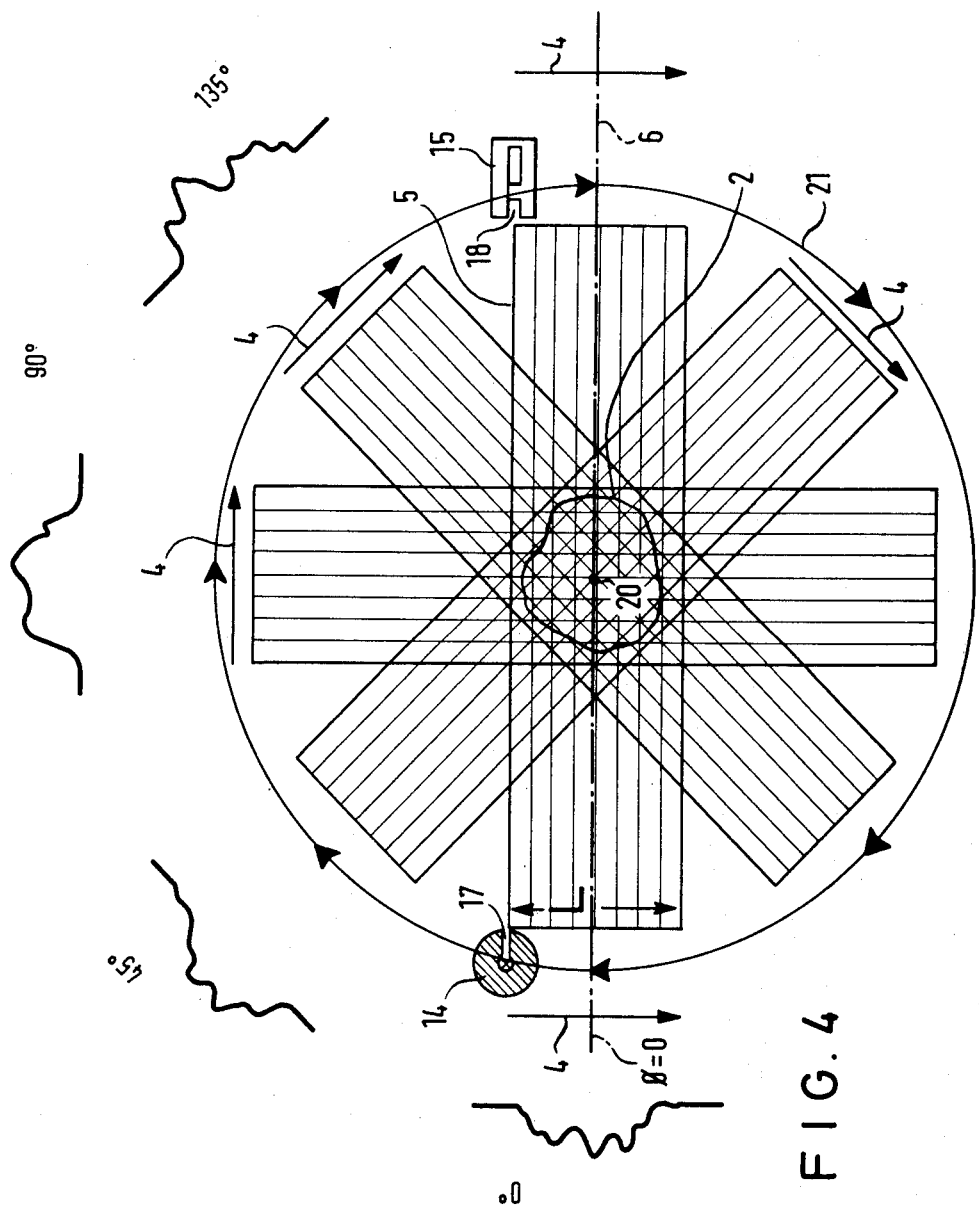
FIG. 4 is an illustration of the various successive measuring operations which are to be carried out with the radiation test arrangement according to FIG. 3.

Reference is made first to FIGS. 1 to 4, of which FIGS. 1, 3, and 4 show schematically an arrangement for carrying out the computer tomography, in particular on tree trunks, for the determination of red rot. This arrangement comprises a measuring system 1, by means of which are determined, through external measurements on the object, e.g. on a tree trunk 2 (see FIG. 3), unidimensional absorption profiles g (1,φ), of which one example is shown in FIG. 2 for better illustration.

These unidimensional absorption profiles, which appear at the output 3 of the measuring device 1, represent the integral or total coefficient of absorption g of the tree trunk 2 for a certain radiation, such as for gamma ray quantums of 60 keV, as a function of the travel distance 1 of a translatory motion 4 of the measuring ray 5, and that at a predetermined, constant angle φ of the measuring ray 5 relative to an arbitrarily fixed zero direction 6.

These unidimensional absorption profiles g (1,φ) are measured for several angles φ, for instance, as illustrated in FIG. 4 which shows the measuring arrangement successively turned by 90° as compared to FIG. 3, for the angles φ of 0° and 45°; 90° and 135°, as the profile examples shown in FIG. 4 are to indicate also.

After suitable processing, smoothing and digitalization the unidimensional profiles g (1,φ) are entered in a digital computer 7 and stored there in a memory 8 connected to the digital computer 7. The digital computer 7 is further provided with a programming unit 9, via which it receives a suitable program so that, from all stored unidimensional profiles g (1,φ) of the total coefficient of absorption, two-dimensional displays of the position-dependent coefficient of absorption $\mu$ (x,y) are available at the output of the digital computer 7. In the present case, the digital computer 7 has two outputs 10, 11, the former being connected to a printer 12 and the latter to a visual and/or display unit 13.

Figure 7:
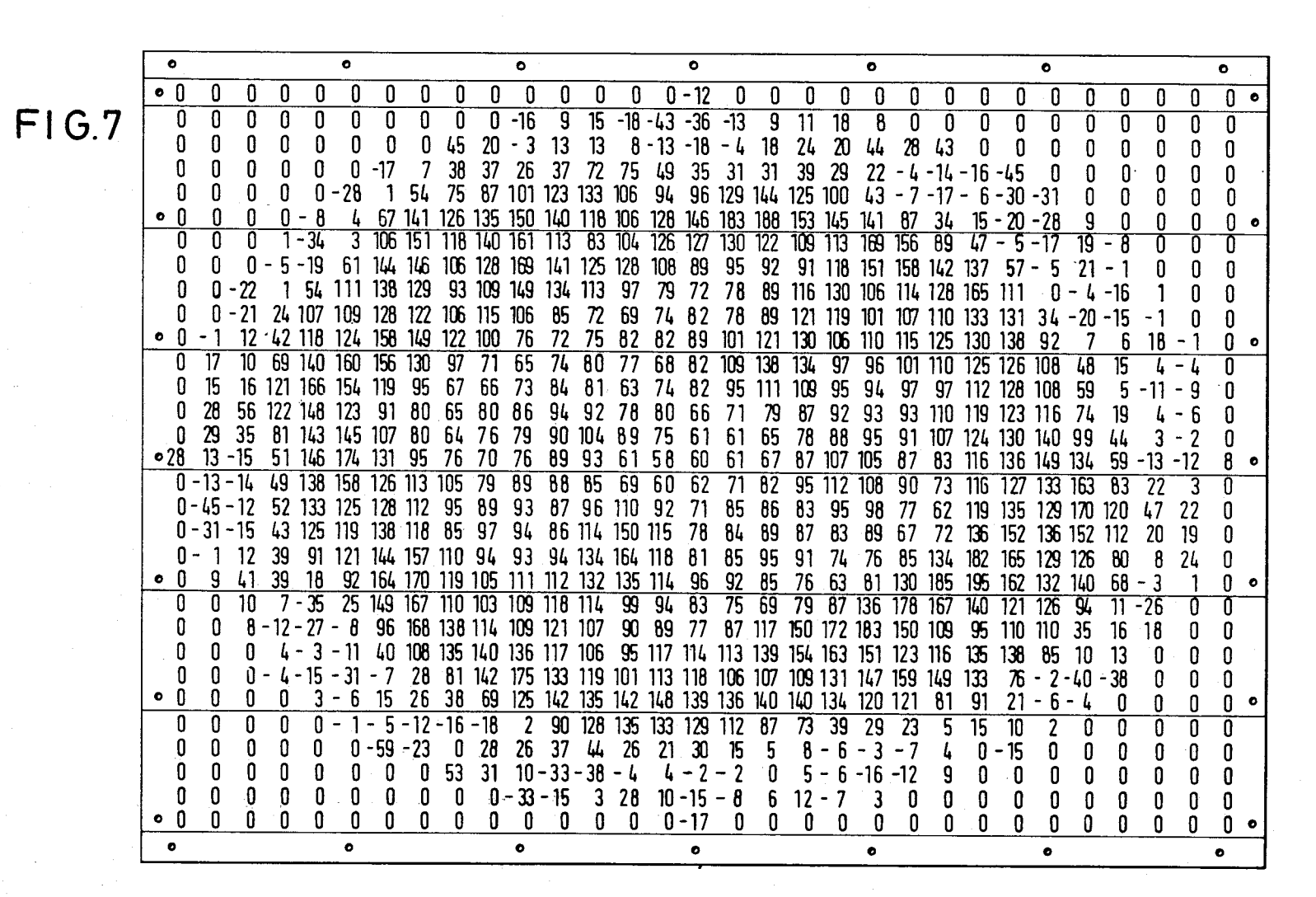

At the printer a number matrix is obtained of the coefficients of absorption $\mu$ (x,y) on one transverse trunk section of the tree tested. An example of such a numbers matrix, which was obtained by gamma radiation of Americium 241 and is true to scale, is shown in FIG. 7. Each numerical value of this number matrix is a measure of the absorption of the gamma radiation by the wood or the substance of the tree trunk tested at the point of the trunk cross-section where this numerical value appears.

Figure 8:
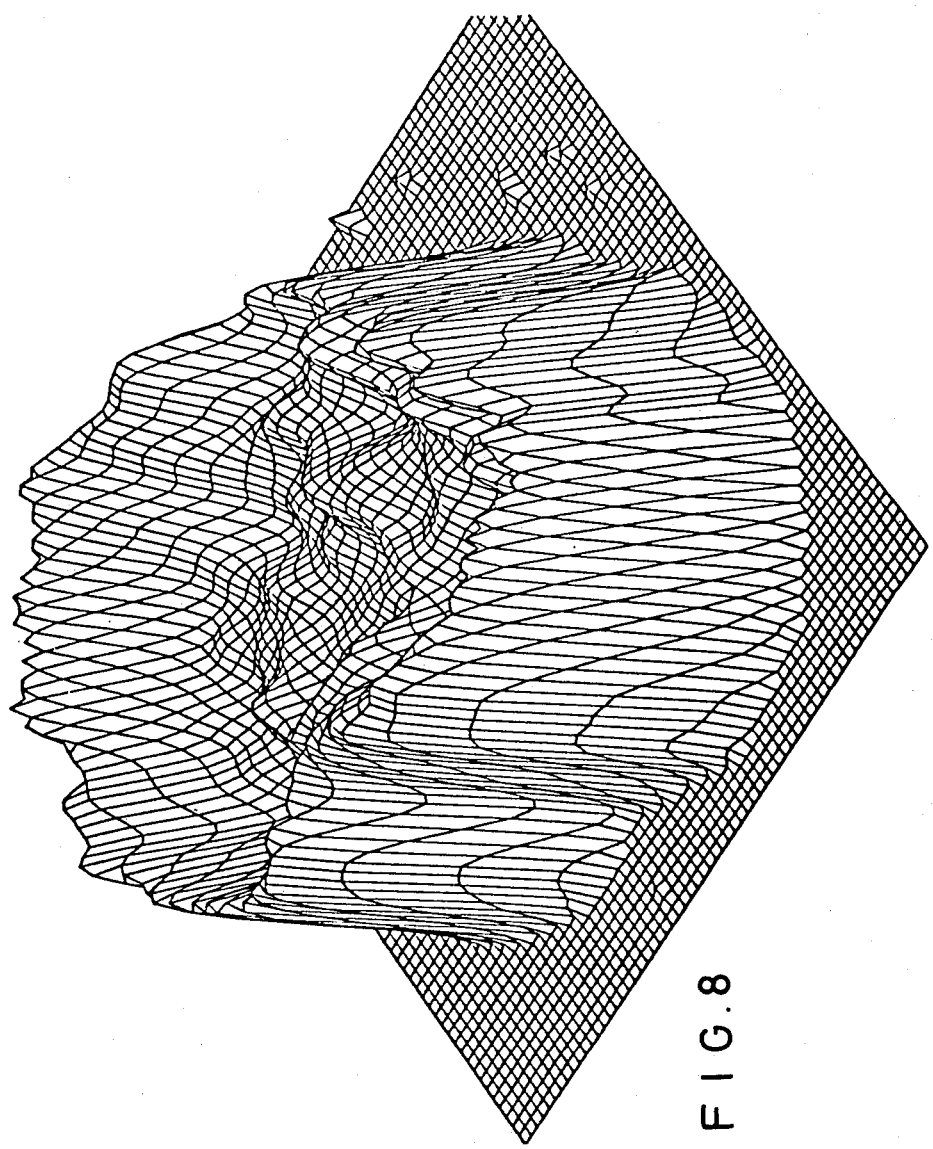
FIG. 8 is an example of a three-dimensional graph of the coefficients of absorption of the various points of a transverse tree section, generated from a number matrix of the kind shown in FIG. 7.
Figure 9:
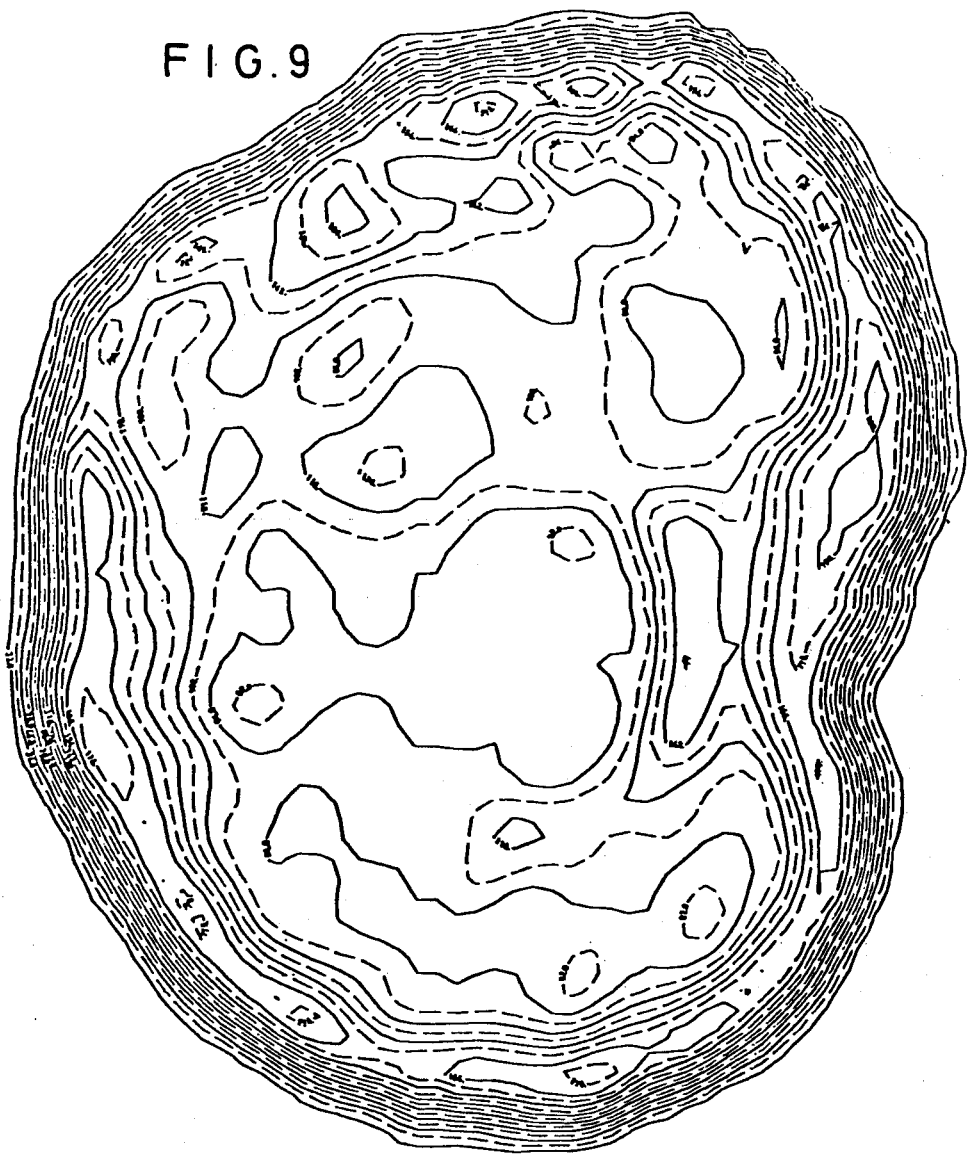
FIG. 9 is an example of a chart of the measured coefficients of absorption in the form of contour lines.

The visual and/or display unit 13 may be a plotter or graph, for instance, or another display instrument of the kind which gives a pictorial representation of the position-dependent coefficient of absorption $\mu$ (x,y) in three-dimension form, of which one example is illustrated in FIG. 8, or as contour line chart, of which an example is shown in FIG. 9.

Figure 10:
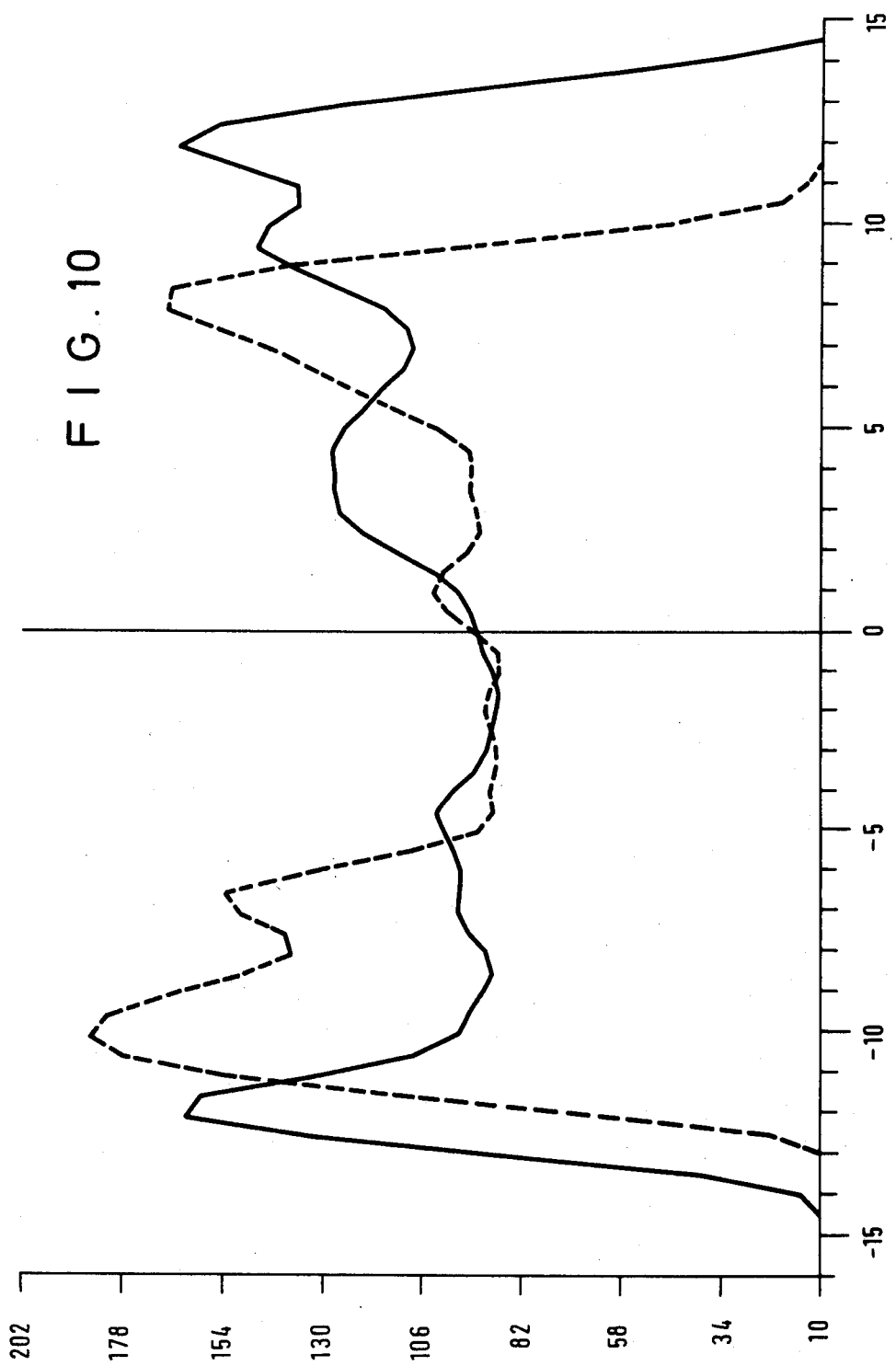
FIG. 10 is an example of a graph of two sections perpendicular to each other through the center of the reconstruction according to FIG. 8.

A comparison of FIGS. 8 and 9 will readily reveal the interrelationship between these two modes of representation, as both Figures show how the position-dependent coefficient of absorption $\mu$ (x,y) varies in the same sectional plane of the same tree trunk. FIG. 10 depicts two sections perpendicular to each other, the one being shown in solid, the other in broken lines, through the center of the reconstruction per FIG. 8.

The visual and/or display unit 13 may also have a screen of a television tube for display, or any other suitable device for the graphic representation of the two-dimensional course of the position-dependent coefficient of absorption $\mu$ (x,y).

Figure 5:
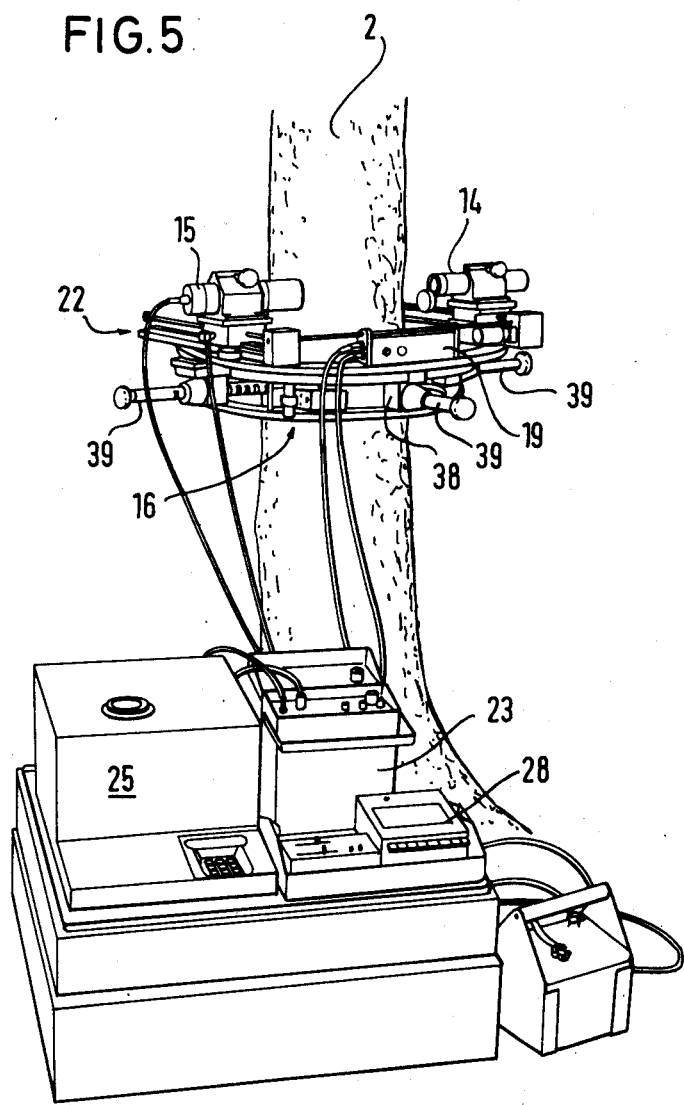
FIG. 5 is a perspective view of the mobile device shown in FIG. 3 on a tree trunk being examined with it.
Figure 6:
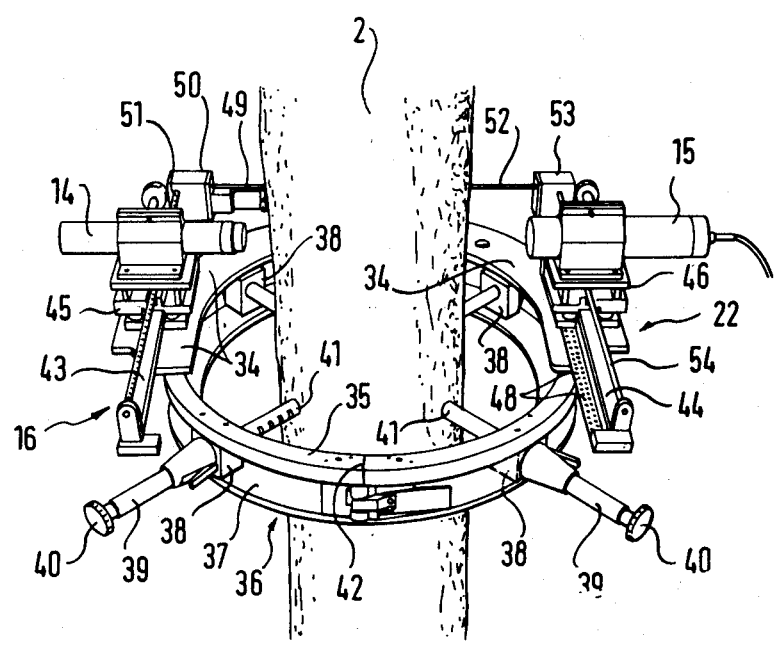
FIG. 6 is a partial view of the mobile device according to FIG. 5 in perspective view.

Now that the entire arrangement for the execution of computer tomography, in particular on tree trunks, has been explained above, the following will explain greater detail individual components of this arrangement, especially of a mobile measuring device 1, the principle of which is shown in FIGS. 3 and 4, and a perspective view in FIGS. 5 and 6.

As schematically shown in FIG. 3, the measuring device generally depicted by the numeral 1 comprises a radiation source 14 which emits a test beam 5 as a narrow bundle of rays through a limited field. Opposite the radiation source 14 is a detector 15, located on the side of tree trunk 2 which faces away from the radiation source 14 so that the test beam 5 passes through the tree trunk 2 and its intensity, weakened by absorption in the tree trunk, is then measured by the detector 15, which is, for example, a scintillation detector or another detector sensitive to the respective radiation of the radiation source 14.

The radiation source 14 and the detector 15 are mounted on a common frame 16 so that the beam aperture 17 of the radiation source 14 and the beam entry opening 18 of the detector 15, and thus also the test beam 5 running between the two, lie in one test plane which is perpendicular to the lengthwise direction of the tree trunk 2 and identical with the drawing plane of FIGS. 3 and 4. In addition, the radiation source 14 and the detector 15 are mounted on the frame 16 so that the beam aperture 17 and the beam entry opening 18 can be moved parallel to and synchronous with each other in the test plane when the translatory motion 4 is performed. This motion is brought about by an electric motor 19, for instance. The maximum length L of the translatory motion is slightly greater than the maximum diameter of the tree trunk 2 in the test plane so that a complete unidimensional profile $(1,\phi)$ covering the entire cross-section of the tree trunk can always be measured.

Furthermore, the frame 16, together with the radiation source 14 and the detector which are rigidly joined mechanically together in relation to each other and movable in the manner described above, is in turn rotatable about an axis 20 extending perpendicular to the test plane and preferably identical with the imaginary and idealized center axis of the tree trunk 2 so that the test beam 5 can be sent through the tree trunk 2 in the test plane at a great variety of angles $\phi$ relative to the zero direction 6. The rotary motion 21 about the axis 20 is shown by appropriate arrows 21.

As already indicated above, FIG. 4 shows four different rotary positions of the frame 16, and hence of both the radiation source 14 and the detector 15, and in each of these rotary positions both the radiation source 14 and the detector 15 perform a translatory motion 4, whereby a unidimensional profile g $(1,\phi)$ each for the four values of $\phi$ indicated above is taken. In other words, the frame 16 is rotated stepwise by a predetermined angle of rotation $\Delta\phi$, comes to a standstill after each step, and during the standstill period a translatory motion 4 takes place. This translatory motion may either be continuous, in which case a digitalization of the unidimensional profile is required before the latter is entered into the digital computer 7; but the translatory motion 4 may also take place stepwise.

For the purpose of length coordination the quantity e (see above) is measured at the same time by means of a length measuring device 22 which is schematically indicated in FIG. 3.

As seen in FIG. 3, the mobile measuring device comprises a portable assembly in which the generally stationary digital computer digital computer 7 is permitted to be carried anywhere in the wood, on any terrain, mountain, or the like where trees stand. In addition to the above described test sensor consisting essentially of the radiation source 14, the detector 15, the frame 16, the motor 19, a fastening mechanism is provided, described below in greater detail, for fastening the frame 16 to the tree trunk 2 to be tested. For actual data determination, a pulse counter 23 is connected to the detector 15 and furnishes corresponding electrical pulses which are a measure of the radionuclide radiation impinging the detector 15, radionuclides being generally used to generate the test beam 5 in the radiation source 14. The pulse counter 23 is connected via a line 24 to the microprocessor and memory unit 25 and in addition, the length measuring device 22, which is provided partly on the frame 16 and partly on the housing of the detector 15, is connected through its part attached to the housing of the detector 15, to the microprocessor and memory unit 25 via a line 26, as is the motor 19 which is connected to the microprocessor and memory unit 25 via a line 27 so that it can be controlled by the latter in which, by the way, the batteries for the operation of the entire measuring device are also accommodated.

The test data, the determination of which is controlled by the microprocessor and memory unit 25 and which are stored in the latter, are recorded by means of a commercial magnetic tape cassette recorder 28 connected to the microprocessor and memory unit 25 via the line 29 so that they can be transported readily to the stationary digital computer 7.

In addition to the computer 7, the memory 8, the programming unit 9 containing the reconstruction program, the printer 12 and the visual and/or display unit 13 which have already been discussed above in connection with FIG. 1, the stationary installation may also comprise a tape punch 30, if the test results are to be entered via punched tapes into the memory 8 of the computer 7. This tape punch may also be connected directly to the microprocessor and memory unit 25 of the mobile measuring device 1, if the punched tapes containing the test data are to be generated directly without recording them first on a magnetic tape cassette by the magnetic tape cassette recorder 28. For this purpose, the tape punch 30 may be connected directly to the microprocessor and memory unit 25, as indicated by the line 31. A battery charger 32 serves to recharge batteries of the mobile measuring device 1 via the line 33 upon its return after being used.

However, the computer together with the memory 8, the programming unit 9, the visual and/or display unit 13 and possibly also both the printer 12 and the tape puncher 30 may also be included in the mobile measuring device, in particular by housing these components in a motor vehicle such as four-wheel drive vehicle, a VW bus or the like, and operating them through batteries or, if necessary, through the light or other generator driven by the engine of the motor vehicle.

In FIGS. 5 and 6, the mobile measuring device 1 is depicted as applied to a tree trunk 2, FIG. 5 giving an overall view while FIG. 6 shows in some more detail only the part of the measuring device attached directly to the tree trunk. Only this latter part is described below in greater detail because the rest of the measuring device 1 has already been described at length above.

As may be seen from FIG. 6, the frame 16 comprises a plate 34 of roughly semicircular ring shape, on which are mounted the radiation source 14, the motor 19 (see FIG. 5, because in FIG. 6 this motor is hidden behind the tree trunk), the detector 15 and the length measuring device 22, and this frame is mounted via slide shoes or otherwise on a circular guide rail 35 for its rotary motion 21 about the axis 20 of the tree trunk 2.

Disposed on the plate 34, parallel to each other and on diametrically opposite sides, are guide rails 43 and 44, on each of which a carriage 45, 46 is movably mounted. The radiation source 14 is provided on the first carriage 45, and the detector 15 as well as one part of the length measuring device 22 is provided on the second carriage 46, while the other part of the length measuring device 22 is located on the guide rail 44 at 47. In the example shown, the latter part 47 of the length measuring device 22 consists essentially of a perforated rail and an elongated, in particular stripeshaped infrared light source disposed below the perforated rail with reference to the picture of FIG. 6, so that infrared light is radiated in an upward direction through each of the holes 48 of the perforated rail, which holes are evenly spaced from each other. This infrared light is detected by the part of the measuring device located on the carriage 44, which part comprises an infrared detector when this infrared detector, which can only pick up the infrared light of a single hole at a time, arrives over one of these holes 48. Through a pulse counter connected to the infrared detector not visible in detail in the drawing, the length measuring device receives pulses so that the length position of the detector 15, and hence that of the radiation source 14, along the travel distance 4 can be determined by the number of pulses. In addition, these pulses can be utilized to control the motor 19 in order to incrementally stop the latter at each hole until the respective radiation measurement in this position has been carried out.

The motor 19, not visible in FIG. 6 (but seen in FIG. 5), is connected to the carriage 45 via a first output shaft 49 and a first gear box 50 provided at the one end of the guide rail 43, and via a threaded carriage drive spindle 51 which emanates from the latter and is mounted at the other end of the guide rail 43. The external thread of the spindle is in engagement with a nut, threaded bushing or the like (not shown) fixed to the carriage 45. To drive the carriage 46 there is provided on the motor 19, in identical structural arrangement and function, a second output shaft 52 which is connected, via a second gear box 53 of the same design as the first gear box 50, to a second threaded carriage drive spindle 54 whose threaded portion is likewise in engagement with a nut, threaded bushing or the like (not shown) fixed to the carriage 46.

The annular guide rail 35 forms part of the fastening mechanism 36 with which the frame 16 is fastened to the tree trunk 2. In detail, this fastening mechanism comprises a circular supporting band 37, provided so as to be spaced from and parallel to the guide rail 35 and connected to the latter by connecting webs 38 which, in turn, are distributed, preferably at uniform spacing, over the circumference of the guide rail 35 and supporting band 37. Mounted in some of these webs is a fastening bolt 39 which extends radial to the guide and supporting rail 35 and band 37 and is in screw engagement with a bearing so that its front end 41 can be caused to contact in its longitudinal direction the tree trunk 2 by turning its handle 40. Since three or four fastening bolts 39 evenly distributed over the circumference of the guide and supporting rails 35, 37 are provided, the fastening mechanism 36 can be effectively clamped to the tree trunk 2, as may be seen particularly well in FIG. 6.

The guide rail 35 and supporting band 37 are cut through radially at two opposite points so that they are composed of two semicircular parts each so that they can be easily arranged around the tree trunk 2 and the connected to each other at these points. One of these parting points 42 is visible in FIG. 6. Fastening the two semicircular parts of the fastening mechanism 36 to each other can be accomplished in any suitable manner by means of screws, quick-release fasteners, or the like.

Figure 11:
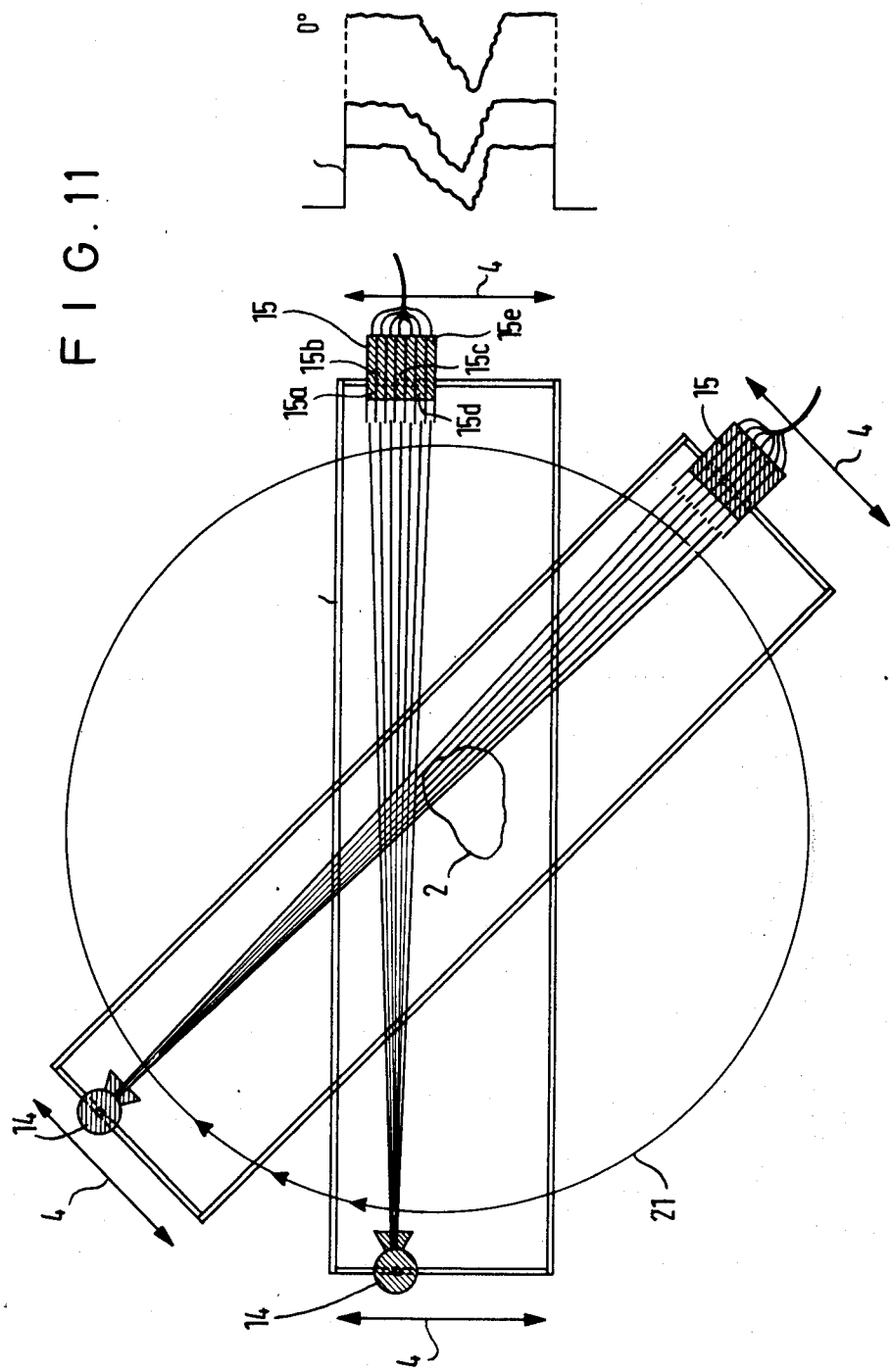
FIG. 11 is a first modified embodiment of the radiation measuring arrangement shown in FIGS. 3 and 4.

In FIGS. 11 and 12 are shown two midified embodiments of the assembly of the radiation source 14, detector 15 and frame 16, permitting a faster measurement and hence a considerable shortening of the measuring time. Shown are two measuring positions each of the radiation source 14, the detector 15 and the frame 16.

The embodiment according to FIG. 11 is characterized in that the detector 15 consists of several individual detectors 15a, 15b, 15c, 15d, and 15e, juxtaposed in the direction of the translatory motion 4 so that in one position of the detector along its translatory travel path 4 a multiplicity of test points are covered. This requires, for instance, the movement of the detector 15 only in two or three steps along the translatory travel path 4 to cover the entire tree trunk 2 and take a measurement at a certain angle $\phi$.

In the embodiment example according to FIG. 12, the detector 15 also consists of many individual detectors 15a to 15z. These individual detectors 15a to 15z disposed in a circular arc being selected so that the transverse section of the entire tree trunk 2 is completely covered every time at a certain angle $\phi$, therefore, no translatory motion whatever is necessary, only a rotary motion 21.

It goes without saying that the test beam 5 must be a divergent beam or a "beam fan" in the cases of FIGS. 11 and 12 to penetrate the tree trunk 2 in a certain cross-sectional area or in the entire cross-section and to cover all detectors 15a to 15e or 15a to 15z.

By way of example, data on the construction of an embodiment example of the equipment according to the invention and of the execution of the method according to the invention are given.

14 mCi of the radionuclide Am-241, which emits gamma quantums of an energy of 60 keV, serve as radiation source. The radiation, weakened by the tree trunk, is picked up by a scintillation detector. A gap 5 mm wide and 18 mm high is masked out of the cone of radiation in front of the detector by means of a lead collimator. Radiation source and radiation receiver run on rails and are moved jointly by a motor in translatory direction. The rotary motion of 15° each can be brought about by means of a motor or manually with the aid of a degree scale. This measuring arrangement is placed on a mounting structure which is clamped to the tree. Trunks up to 40 cm diameter were tested. Coupled to the translatory motion of the detector is an infrared light barrier which moves over a stationary, perforated rail having a 2.5 mm grid and serving the determination of the location of an absorption measurement.

The entire data pickup is controlled by a microprocessor system, "Intercept Jr.", of the Intersil company of the PDP-8E instruction code. The microcomputer and the electronic matching systems developed according to the invention are designed in CMOS technology so that they are characterized by little current consumption and uncritical voltage supply from a 6 V lead battery. The memory comprises 4 K words at 12 bit, 1 K thereof being occupied by a fixed operating program in read-only memory. The data pickup program requires 1 K memory so that 2 K are left for the temporary storage of absorption measurements.

As soon as the data pickup program is stored in the memory of the microcomputer, the various subprograms may be started by actuating the operating keyboard. The absorption measurements are taken with pulse preselection so that the test carriages move the slower, the thicker the tree section just being irradiated. This results in a constant statistical error in the entire reconstruction area. Since the position and density resolution requirements are not high, the relative small data store is sufficient for taking a tomogram.

Upon the conclusion of the measurements on a tree, the measured data are rerecorded on a commercial cassette tape recorder; this frees the data store for the next series of data. The program is also on magnetic tape so that it can be reloaded in case of need.

After return from the forest the test data are transferred from the cassette to punched tape under the control of the microprocessor and read into the computer TR 440 in the stationary computer center. The interpretation program according to the reconstruction method by Ramachandran and Lakshminarayanan with addition low-pass filtering computes the coefficients of absorption of the transverse tree section measured as a function of position. The computed values may be displayed as a number matrix on the highspeed printer or graphically as three-dimensional picture with covered lines or as contour line chart.

The coefficients of absorption of wood or gamma quantums of 60 keV range roughly between 0.05 and 0.2 $cm^{-1}$. The statistical error of the measurements, brought about by the quantum noise, is likewise computed by the interpretation program; it is about 0.001 $cm^{-1}$. FIG. 8 shows the reconstruction of a spruce attacked by red rot. The coefficients of absorption decrease from about 0.18 $cm^{-1}$ at the edge to about 0.05 $cm^{-1}$ at the diseased spots at a statistical reconstruction error of 0.0012 $cm^{-1}$.

The measuring time can be shortened with equipment which operates with several radiation detectors simultaneously and can girdle thick trees. The measuring time is further reduced by the use of a radionuclide of greater quantum energy. For reasons of radiation protection and weight energies up to 300 keV may be used.

Furthermore, measurements may be carried out in which the radiation source used is not a gamma-radiating radionuclide, but a neutron source. This makes it possible to determine the absorption of neutrons in corresponding manner in a layer at each individual location and obtain information in particular on the hydrogen or moisture content of the substance. Also possible are simultaneous absorption measurements of gamma and neutron rays to gain additional information for additional evidence on the interior of the objects.

By using different radionuclides, i.e. by measuring the coefficients of absorption for different radiation energies, information on th chemical composition at the various spots of the respective transverse section can be gained. For this purpose the same measurements must be taken with rays of different energy. The method remains unchanged, merely the equipment is supplemented by a double radiation source and by discriminators in conjunction with the detectors.

The method described and the equipment for its execution may be employed and not only for the detection of red rot and other tree diseases on the standing trunk, rather, it is basically possible to take with it measurements of the coefficient of absorption at all points which—for whatever reasons—are inaccessible. Moreover, they also are of practical significance for routine use not only in the forestry and lumber industries, but also for monitoring the state of health of city and park trees, of trees alonside roads and in the vicinity of parking lots, etc. They also make possible the non-destrictive testing of concrete columns to check them for cavities, or of the type and fit of steel armor. Other application examples are the testing of pipes and lines which should not be opened for reasons of risk or for economic reasons, in order not to interrupt the operations.

What is claimed:

1. A method for the non-destructive testing of immobile objects such as for disease in living trees, or the like comprising the steps of mounting on one side of said object a portable source of radiation and on the opposite side of said obejct a portable detector for such radiation, indexing said source and said detector cooperatively about said object through a plurality of positions in a given cross-sectional plane, passing a beam of predetermined radiation through said object and detecting the beam at each of said positions, determining responsive to said detection the coefficient of absorption of radiation of said object, and converting said coefficient of absorption at each of said positions into a computerized tomographic display.

2. The method according to claim 1, wherein said radiation source is gamma, X-Ray or neutron rays.

3. The method according to claim 1, wherein said radiation source is a gamma ray emitting nuclides not exceeding about 300 keV selected from the group consisting of gamm HG-203 and gamma Am-241.

4. The method according to claims 1, 2, or 3, wherein the object to be tested is a tree and the radiation source comprises at least one beam directed in a plane substantially perpendicular to the longitudinal axis of the object to be tested.

5. The method according to claim 4, wherein said at least one beam is applied sequentially about the circumference of said object in said predetermined cross-section.

6. The method according to claim 5, wherein a plurality of beams are passed in a predetermined box through said object and simultaneously sensed, said beams being subsequently indexed about the axis of the object until the entire circumference is traversed.

7. Apparatus for the non-destructive testing of immobile objects such as for disease in living trees comprising a supporting frame adapted to be removably mounted on said object to be tested, a source of radiation and a detector for said radiation mounted to pass a beam of said radiation through said object, means responsive to said detector for measuring the coefficient of absorption of said source by said object and computer means for displaying tomographically said coefficient of absorption.

8. The apparatus according to claim 7, wherein said supporting frame includes fastening means for rotatingly mounting said source and director of radiation for movement about the axis of said object.

9. The apparatus according to claim 8, wherein the fastening means comprises a circular guide band, on which the supporting frame is mounted, said band being movable about the circumference of said object.

10. The apparatus according to claim 9, wherein said circular guide band is divided into several parts of a circular sector shape and includes means for fastening said parts to each other for rigging the guide band around the object.

11. The apparatus according to claim 9, wherein said rigging means comprises a plurality of threaded bolts mounted in a threaded bore of said guide band to extend in their lengthwise direction radial to the guide band and be adjustable in their lengthwise direction whereby their ends facing the object can be caused to rest against the latter.

12. The apparatus according to claim 11, wherein said bolts are evenly distributed over the circumference of the circular guide rail and at leaast three fastening bolts are provided.

13. The apparatus according to claim 9, wherein said supporting frame has a parallel supporting rail which is spaced from the guide band, said supporting rail being divided into several sections of circular segment shape and having connecting webs, on which the fastening bolts are disposed.

14. The apparatus according to claim 7, wherein said radiation source and detector are mounted on a semicircular plate, on which are disposed, parallel and diametrically opposed to each other, two guide rails, a first carriage mounted on rails, so as to be movable lengthwise therealong and a second carriage mounted on the other of said guide rails so as to be movable lengthwise therealong, the radiation source and detector being mounted respectively on said carriages.

15. The apparatus according to claim 14, including a motor disposed on the semicircular plate between the two guide rails, means connecting said motor to each of said carriages, comprising an output shaft, a gear box each provided at one end of each guide rail and a threaded drive spindle emanating from each of the respective gear box and mounted on the respective other end of the guide rail, a nut, and a threaded bushing which is fixed to the respective carriage in engagement with the respective drive spindle whereby said carriages are movable conjointly.

16. The apparatus according to claim 15, including a measuring device to determine the length of movement of said carriage along said guide rail.

17. The apparatus according to claim 15, wherein said measuring device comprises a stationary perforated rail, and an infrared radiation source and an infrared detector movable together with the radiation source or the detector, on opposite sides of said rail.

18. The apparatus according to claim 17, wherein said infrared radiation source is disposed on said perforated rail, said rail being disposed in the vicinity of one of the guide rails, and the infrared detector is mounted on the carriage movable on this guide rail.

19. The apparatus according to claim 16, wherein said radiation source comprises two or more juxtaposed radiation sources.

20. The apparatus according to claim 19, wherein at least one of the radiation sources is a Roentgen or gamma radiation sources and another one of these radiation sources is a neutron radiation source.

21. The apparatus according to claim 19 or 20, wherein several detectors are provided next to each other in opposition to said sources.

22. The apparatus according to claim 20, wherein the detectors are in arcuate fashion and provided in such a number as to cover the entire cross-sectional area intended to be tested.

* * * * *